(12) United States Patent
Brown et al.

(10) Patent No.: US 6,388,816 B2
(45) Date of Patent: May 14, 2002

(54) MULTI-LEAF COLLIMATOR

(75) Inventors: Kevin John Brown, Horsham; Christopher John Snook, Crawley; William Richard Harwood, Hassocks, all of (GB)

(73) Assignee: Elekta AB, Stockholm (SE)

( * ) Notice: Subject to any disclaimer, the term of this patent is extended or adjusted under 35 U.S.C. 154(b) by 0 days.

(21) Appl. No.: 09/791,039

(22) Filed: Feb. 22, 2001

(30) Foreign Application Priority Data

Apr. 28, 2000 (GB) .............................................. 0010235

(51) Int. Cl.⁷ .......................... G02B 27/30; G21K 1/02; G21K 1/04
(52) U.S. Cl. ......................... 359/641; 378/147; 378/152
(58) Field of Search .......................... 359/641; 378/147, 378/149, 152; 250/505.1

(56) References Cited

U.S. PATENT DOCUMENTS

| | | | |
|---|---|---|---|
| 5,166,531 A | * 11/1992 | Huntzinger | 250/505.1 |
| 5,351,280 A | 9/1994 | Swerdloff et al. | 378/65 |
| 5,591,983 A | 1/1997 | Yao | 250/505.1 |
| 5,757,881 A | * 5/1998 | Hughes | 378/65 |
| 6,266,393 B1 | * 7/2001 | Ein-Gal | 378/152 |

FOREIGN PATENT DOCUMENTS

EP       0 314 214 A      5/1989
WO       WO 99/17305      4/1999

* cited by examiner

*Primary Examiner*—Ricky Mack
(74) *Attorney, Agent, or Firm*—Kinney & Lange, P.A.

(57) ABSTRACT

A collimator for a therapeutic linear accelerator comprising first and second opposed arrays of individually longitudinally moveable elongate leaves, and a blocking element arranged transverse to the two arrays and moveable in that transverse direction, thereby to move into a gap between the tips of a leaf from the first array and a leaf from the second array. The blocking element and the two arrays can be in the same plane, thereby reducing the overall height of the device. As the tips of the leaves are usually profiled, it is preferred that the side edges of the blocking element are profiled to a complementary shape. The side edges of the leaves are usually non-vertical in order to allow for the divergence of the radiation beam. Each leaf will have a different angle. Accordingly, it is preferred that the tip of the blocking element has a variable angle, in order to match the angle of whichever leaf is adjacent. This could be achieved, for example, by making at least the tip in a laminar fashion so that each lamination can slide to form a tip which is angled. Alternatively, a rotatable element could be incorporated into the tip. It is also preferred that the blocking element has a flange which extends from a side thereof, positioned to extend adjacent over the tolerance gap between the blocking element and the leaf. It is obviously preferred if there are two blocking elements, disposed on opposite sides.

8 Claims, 2 Drawing Sheets

MULTI-LEAF COLLIMATOR

FIELD OF THE INVENTION

The present invention relates to a multi-leaf collimator (MLC), such as the type commonly used in therapeutic linear accelerators.

BACKGROUND OF THE INVENTION

In a conventional MLC, an array of parallel leaves move longitudinally alongside each other to define a irregular edge. A pair of such arrays are provided in a mutually opposing arrangement such that the pair together define a variable shape aperture which can then define a therapeutic dose of radiation. Diaphragms above or below the leaves can be moved into and out of the area covered by the array to reduce leakage between adjacent leaves.

Several factors mean that the construction and use of an MLC is not as simple. One such factor is that the tips of the leaves generally need to be profiled in order to give a constant and predictable penumbra, which means that an opposing pair cannot be brought into close enough contact to reduce leakage between the gap to an acceptable level.

SUMMARY OF THE INVENTION

The present invention therefore provides a collimator comprising first and second opposed arrays of individually longitudinally moveable elongate leaves, and a blocking element arranged transverse to the two arrays and moveable in that transverse direction, thereby to move into a gap between the tips of a leaf from the first array and a leaf from the second array.

The blocking element and the two arrays can be in the same plane, thereby reducing the overall height of the device.

As the tips of the leaves are usually profiled, it is preferred that the side edges of the blocking element are profiled to a complementary shape.

The side edges of the leaves are usually non-vertical in order to allow for the divergence of the radiation beam. Each leaf will have a different angle. Accordingly, it is preferred that the tip of the blocking element has a variable angle, in order to match the angle of whichever leaf is adjacent. This could be achieved, for example, by making at least the tip in a laminar fashion so that each lamination can slide to form a tip which is angled. Alternatively, a rotatable element could be incorporated into the tip.

It is also preferred that the blocking element has a flange which extends from a side thereof, positioned to extend adjacent over the tolerance gap between the blocking element and the leaf.

It is obviously preferred if there are two blocking elements, disposed on opposite sides.

BRIEF DESCRIPTION OF THE DRAWINGS

Embodiments of the present invention will now be described by way of example, with reference to the accompanying figures, in which.

DETAILED DESCRIPTION OF THE PREFERRED EMBODIMENTS

Figure 1:
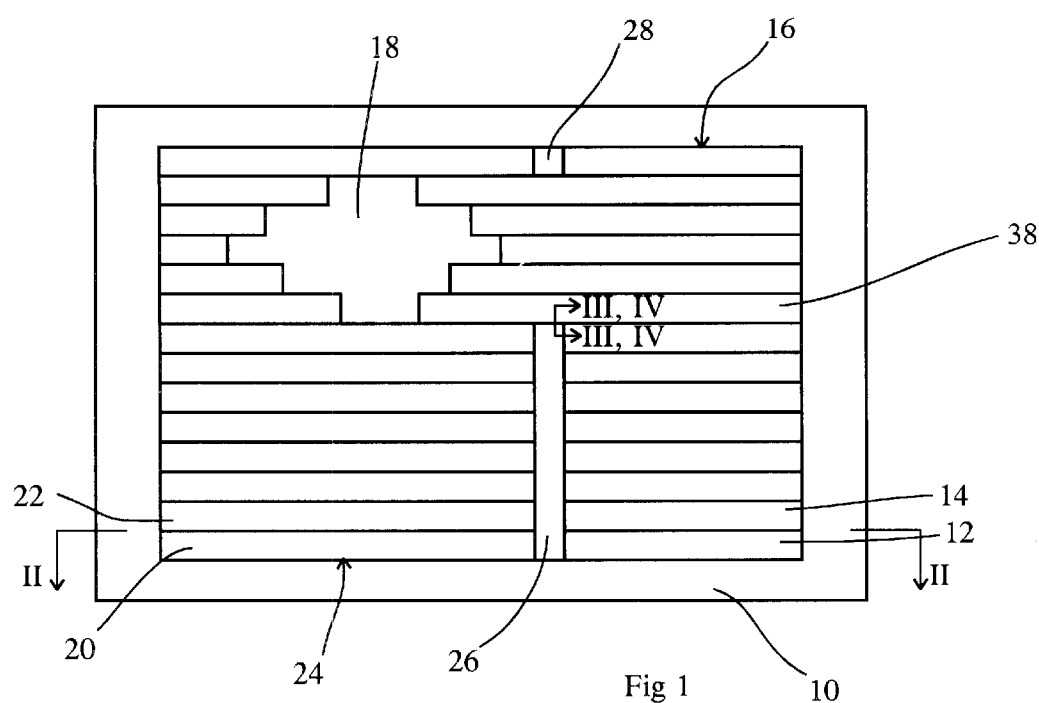
FIG. 1 is a plan view of a first embodiment of the present invention.
Figure 2:
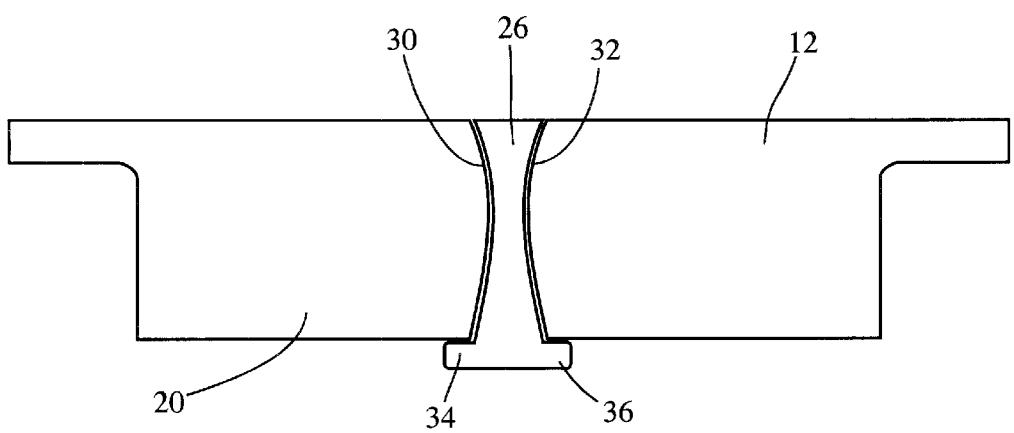
FIG. 2 is a section on II—II of FIG. 1.

Referring to FIGS. 1 and 2, a frame 10 supports a plurality of leaves 12, 14 etc in a first array 16 which are able to slide longitudinally alongside each other to define an edge of a radiation field 18. Likewise, a plurality of leaves 20, 22 etc in a second array 24 slide to define an opposite edge of the radiation field. A multi-leaf collimator of this type is well known.

According to the present invention, a blocking element 26 is supported by the frame 10 and able to extend into the plane of the leaf arrays 16, 24 transverse to the direction of motion of the leaves. A corresponding element 28 is able to extend into the arrays from the opposite side. Thus, in areas where no irradiation is needed, the individual leaves can be extended so as to meet the blocking element 26 (or 28). As shown in FIG. 2, the tips of leaves 12, 20 are profiled so as to provide a stable penumbra and hence the leaves cannot be brought into direct contact as this will leave a distinct gap. The blocking element 26 shown in FIG. 2 has profiled side edges 30, 32 to match the tips of the leaves 12, 20 which abut it.

FIG. 2 also shows a flange 34, 36 which extends transversely from each side of the blocking element to lie beneath the relevant leaf 12, 20. This therefore extends over the tolerance gap which must lie between the blocking element and the leaf and prevents leakage.

Figure 3:
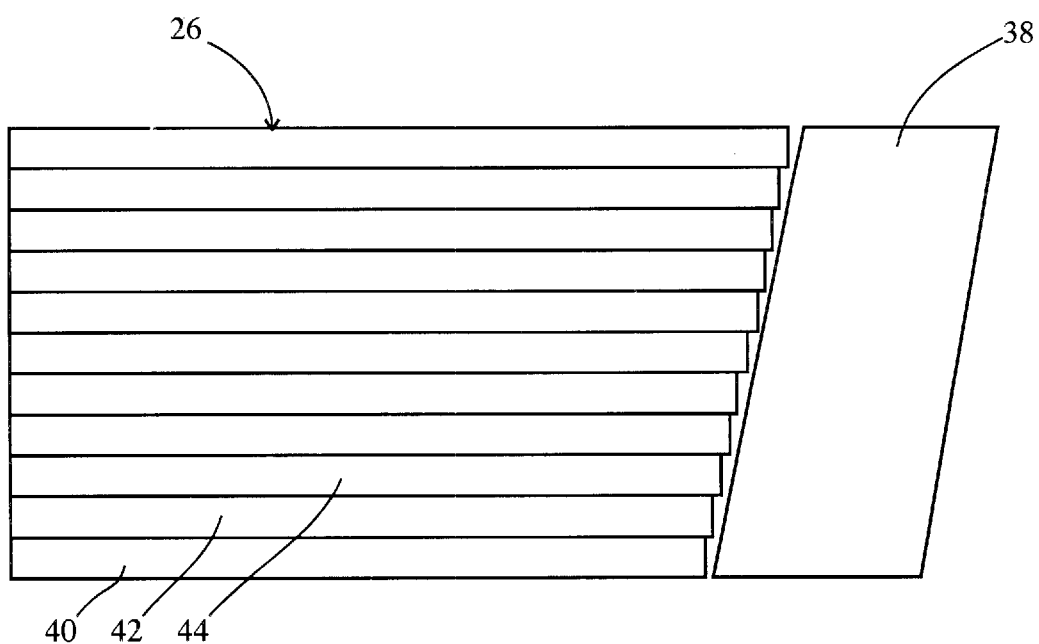
FIGS. 3 and 4 are enlarged views of the tip of a blocking element according to a second and third embodiment respectively.
Figure 4:
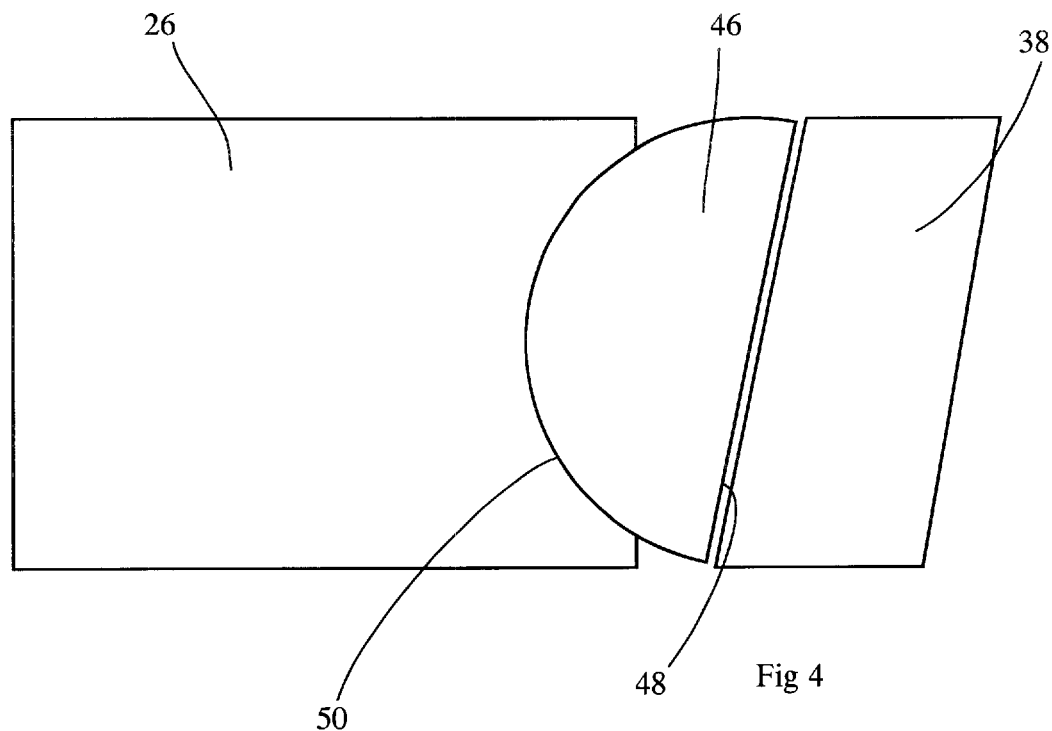

It is usual to form individual leaves with inclined edges such that the edges are substantially aligned with the radiation source. As the source is a point source which emits a divergent beam, each leaf will be inclined by a slightly different amount depending on its location. FIGS. 3 and 4 show designs of the blocking element which are able to cope with this.

In FIG. 3, a tip portion (at least) of the blocking element is form as a laminate of horizontally disposed layers 40, 42, 44 etc. As the blocking element is brought into contact with the side of the leaf 38, the layers 40 etc slide relative to each other to accommodate the inclination of the leaf edge.

In FIG. 4, a further tip element 46 is present on the blocking element 26. The leading face 48 of the tip element is planar, whilst the rear face 50 is arcuate. In cross-section, the tip element is therefore semicircular. The rear face 50 is seated in a corresponding recess in the tip of the blocking element 26. Thus, as the tip element approaches the inclined side of the leaf 38, the tip element rotates in its seat to align itself automatically.

The movement mechanism for the blocking elements 26, 28 can be adapted from that employed for the leaves of the arrays 16, 24. Accordingly it is a straightforward matter to integrate the invention into an otherwise conventional multi-leaf collimator design. By doing so, a greater range of collimator patterns can be obtained with low leakage and potentially without the height penalty of a series of blocking diaphragms above or below the multi-leaf collimator.

What is claimed is:

1. A collimator comprising a first array of individually longitudinally moveable elongate leaves, and a second array of individually longitudinally moveable elongate leaves, the second array being disposed in an opposed relationship to the first, and a blocking element disposed in a direction transverse to the two arrays and moveable in that transverse direction, thereby to move into a gap between the tips of a leaf from the first array and a leaf from the second array.

2. A collimator according to claim 1 in which the blocking element and the two arrays are in the same plane.

3. A collimator according to claim 1 in which the side edges of the blocking element are profiled to a shape complementary to the tips of the leaves.

4. A collimator according to claim 1 in which the tip of the blocking element has a variable angle, in order to match the angle of an adjacent leaf.

5. A collimator according to claim 4 in which at least the tip of the blocking element is laminar so that each lamination can slide to form a tip which is angled.

6. A collimator according to claim 4 in which a rotatable element is incorporated into the tip of the blocking element.

7. A collimator according to claim 1 in which the blocking element has a flange which extends from a side thereof, positioned to extend adjacent over a tolerance gap between the blocking element and the leaf.

8. A collimator according to claim 1 comprising two blocking elements, disposed on opposite sides.

* * * * *